(12) United States Patent
Sota et al.

(10) Patent No.: US 11,200,673 B2
(45) Date of Patent: Dec. 14, 2021

(54) METHOD FOR ANALYZING LONGITUDINAL PIGMENTED BAND ON NAIL PLATE OR SKIN COLOR HUE FOR DIAGNOSING SKIN DISEASE, AND DIAGNOSTIC DEVICE AND COMPUTER PROGRAM THEREFOR

(71) Applicants: WASEDA UNIVERSITY, Tokyo (JP); SHINSHU UNIVERSITY, Nagano (JP)

(72) Inventors: Takayuki Sota, Tokyo (JP); Atsushi Nakamura, Tokyo (JP); Hiroshi Koga, Nagano (JP)

(73) Assignees: SHINSHU UNIVERSITY, Tokyo (JP); WASEDA UNIVERSITY, Tokyo (JP)

( * ) Notice: Subject to any disclaimer, the term of this patent is extended or adjusted under 35 U.S.C. 154(b) by 226 days.

(21) Appl. No.: 16/616,250

(22) PCT Filed: May 22, 2018

(86) PCT No.: PCT/JP2018/019623
§ 371 (c)(1),
(2) Date: Jan. 29, 2020

(87) PCT Pub. No.: WO2018/216680
PCT Pub. Date: Nov. 29, 2018

(65) Prior Publication Data
US 2020/0311939 A1    Oct. 1, 2020

(30) Foreign Application Priority Data
May 25, 2017    (JP) .............................. JP2017-103524

(51) Int. Cl.
*G06T 7/00* (2017.01)
*G06T 7/90* (2017.01)
(Continued)

(52) U.S. Cl.
CPC .......... *G06T 7/0016* (2013.01); *A61B 5/0077* (2013.01); *A61B 5/1032* (2013.01);
(Continued)

(58) Field of Classification Search
CPC ... A61B 5/0077; A61B 2576/00; A61B 10/00; A61B 5/1032; A61B 5/7485;
(Continued)

(56) References Cited

U.S. PATENT DOCUMENTS

| 2007/0043527 A1 | 2/2007 | Quan et al. |
| 2012/0041275 A1* | 2/2012 | Sota ..................... A61B 5/0077 600/300 |
| 2012/0268462 A1* | 10/2012 | Sota ..................... A61B 5/0077 345/419 |

FOREIGN PATENT DOCUMENTS

| JP | 2012-168181 A | 9/2012 |
| JP | 2013-520274 A | 6/2013 |

(Continued)

OTHER PUBLICATIONS

International Search Report dated Aug. 28, 2018 in International Application No. PCT/JP2018/019623.
(Continued)

*Primary Examiner* — Brenda C Bernardi
(74) *Attorney, Agent, or Firm* — Fox Rothschild LLP

(57) ABSTRACT

An analysis method and a diagnostic device, enabling one to determine whether a longitudinal melanonychia is caused by a malignant melanoma or a benign nevus by correcting color variation in a dermoscopic image through standardization of color balance without depending on an imaging device or an operator; and a computer program for allowing a computer to function as the diagnostic device. Proposed is a structure including: an image reading step of reading a color image of a longitudinal melanonychia or an affected skin site of a
(Continued)

subject as a digital color image; an image processing step involving an image size conversion step of converting the whole size of the digital color image into a preset size through pixel size conversion, and a region of interest (ROI)-extraction step of extracting an ROI required for the diagnosis from the digital color image; a chromatic adaptation transformation step of controlling the color balance of the digital color image data through chromatic adaptation transformation; and a discrimination index (DI) calculation step of determining a DI value using the image after the chromatic adaptation transformation.

14 Claims, 5 Drawing Sheets

(51) Int. Cl.
  *A61B 5/00* (2006.01)
  *A61B 5/103* (2006.01)
(52) U.S. Cl.
  CPC .............. *A61B 5/441* (2013.01); *A61B 5/449* (2013.01); *A61B 5/7485* (2013.01); *G06T 7/90* (2017.01); *A61B 2576/00* (2013.01); *G06T 2207/10024* (2013.01); *G06T 2207/30088* (2013.01); *G06T 2207/30096* (2013.01)
(58) Field of Classification Search
  CPC .................... A61B 5/441; A61B 5/449; G06T 2207/30096; G06T 2207/10024; G06T 2207/30088; G06T 7/90; G06T 7/0012; G06T 7/0016; H04N 1/60
  See application file for complete search history.

(56) References Cited

FOREIGN PATENT DOCUMENTS

| | | |
|---|---|---|
| JP | 5600424 | 8/2014 |
| JP | 2016-112270 A | 6/2016 |
| JP | 2016-174671 A | 10/2016 |

OTHER PUBLICATIONS

Koga et al.: "Automated evaluation system of dermoscopic images of longitudinal melanonychia: Proposition of a discrimination index for detecting early nail apparatus melanoma", The Journal of Dermatology 2014, 41: 867-871.

* cited by examiner

METHOD FOR ANALYZING LONGITUDINAL PIGMENTED BAND ON NAIL PLATE OR SKIN COLOR HUE FOR DIAGNOSING SKIN DISEASE, AND DIAGNOSTIC DEVICE AND COMPUTER PROGRAM THEREFOR

CROSS-REFERENCE TO RELATED APPLICATIONS

This application is a § 371 U.S. national phase entry of International Patent Application No. PCT/JP2018/019623, filed May 22, 2018, which claims priority to and the benefit of Japanese Patent Application No. 2017-103524, filed May 25, 2017, both of which are hereby incorporated herein by reference in their entireties.

TECHNICAL FIELD

The present invention relates to a method for analyzing a longitudinal pigmented band on a nail plate or a skin hue for diagnosis of skin diseases, a diagnostic device using the analysis method, and a computer program that causes a computer to function as the diagnostic device.

BACKGROUND ART

A longitudinal pigmented band on a nail plate is a state of black or brown linear or belt-like pigmentation being developed in the longitudinal direction from the basal portion of a nail plate. If there is any lesion present in or near a nail matrix, a longitudinal pigmented band first appears on the surface of the basal portion of the nail plate, and then, as the nail extends, the linear pigmentation gradually moves toward the tip of the nail. Typical lesions that cause the same include a pigmented nevus with an increased melanin deposit, in which a longitudinal melanonychia appears on a nail after the pigmented nevus occurs in a nail matrix. It also appears on a nail as a change due to an early-stage symptom preceding the change of skin pigment after a benign skin tumor, or a malignant skin tumor such as nail apparatus melanoma (subungual melanoma) or pigmented Bowen's disease occurs in a nail matrix. Further, a longitudinal pigmented band appears on a nail after lesions are caused in or in the vicinity of a nail matrix due to skin diseases such as lichen planus and lichen striatus; endocrine abnormalities such as Addison's disease and Cushing's syndrome; metabolic abnormalities such as porphyria and malnutrition; systemic diseases such as Peutz-Jeghers syndrome and pregnancy; bacterial or fungal infectious diseases; internal use of drugs such as anti-cancer drugs; radiation therapy or ultraviolet therapy to the fingers; and repeated external stimulation thereto. In addition, autoimmune skin diseases such as lupus erythematosus exhibit reddish skin symptoms.

A nail apparatus melanoma, also called subungual melanoma, appears when a melanocyte present in a nail matrix cancerates. If it is possible to diagnose it as such at the initial stage of the nail apparatus melanoma, for example, it is expected to increase a 5-year survival rate or prevent a recurrence within 10 years. If the melanocyte is not cancerous, it is considered a benign nevus. It is considered that a pattern of the longitudinal melanonychia is usable to determine whether it is a nail malignant melanoma or a benign nevus. However, in order to determine whether the longitudinal melanonychia is caused by a nail apparatus melanoma or by a benign nevus by visually inspecting the longitudinal melanonychia using a dermoscope or by viewing a dermoscopic image that is a color image of the longitudinal melanonychia, it is necessary for a tester to gain considerable experience, since no clinical differentiation standard has been established yet. For this reason, there have been strong demands from the clinical site for realizing a non-invasive and objective diagnosis to determine whether the longitudinal melanonychia is due to a malignant melanoma or a benign nevus, as well as a diagnostic method for longitudinal melanonychia-related diseases. Furthermore, since the malignant melanoma can be diagnosed not only from a nail plate color but also from a skin color if the pathological condition of the malignant melanoma progresses, it has been required to realize an analysis method for diagnosing the malignant melanoma by way of skin.

To meet such needs, the present inventors developed a diagnostic device where an RGB variable value of each pixel in the dermoscopic image of a longitudinal melanonychia is assumed as a three-dimensional vector in a RGB space; a discrimination index DI is obtained from the latitudinal and longitudinal variables thereof, and the discrimination index DI values are discriminated with a threshold value as a boundary, thereby realizing a noninvasive and objective diagnosis to determine whether the longitudinal melanonychia is a malignant melanoma or a benign nevus (for example, Non-Patent Document 1 and Patent Document 1).

PRIOR ART DOCUMENTS

Non-Patent Document(s)

Non-Patent Document 1: Koga, H., Yoshikawa, S., Sekiguchi, A., et al., Automated evaluation system of dermoscopic images of longitudinal melanonychia: Proposition of a discrimination index for detecting early nail apparatus melanoma, J. Dermatol. 2014; 41: 867-871.

Patent Document(s)

Patent Document 1: JP Patent Publication No. 5600426

SUMMARY OF THE INVENTION

Problems to be Solved by the Invention

As for the diagnostic devices described in Non-Patent Document 1 and Patent Document 1, there have been concerns that the discrimination index DI may be affected by differences in nail plate area extracted for analysis, and variations in color balance which are caused by a photographing device and are latent in an input color digital image such as a JPEG image.

Regarding the differences in nail plate area to be extracted, even if the selection and extraction rules are determined in advance, there will be caused unavoidable differences depending on who are to perform a test.

The color balance of RGB variables of an input color image such as a JPEG image is considered to be likely to vary depending on each photographing device because its dermoscopic illumination device differs from model to model and a photographing camera thereof has a manufacturer's own image processing engine.

From the above-mentioned, it is considered preferable to standardize RGB variables included in a JPEG image as a target for calculation of the discrimination index DI, by using some method.

The present invention has been made in view of such circumstances, and provides an analysis method or a diagnostic method and a diagnostic device that corrects the color tone of dermoscopic images by color balance standardization, allowing analysis or diagnosis to determine whether longitudinal melanonychias are due to malignant melanomas or not without depending on tester or imaging device; and a computer program that causes a computer to function as the diagnostic device.

Means of Solving the Problems

To solve the above problem, the present invention provides a method for analyzing a longitudinal pigmented band on a nail plate and a skin hue for performing: diagnosis of an acral lentiginous melanoma; diagnosis of a skin cancer such as a malignant melanoma on the skin; or diagnosis of an autoimmune skin disease, or for obtaining these diagnosing data, including:

an image reading step of reading a color image of a longitudinal pigmented band on a nail plate or a skin site of a subject as a digital color image;

an image processing step of including an image size conversion step of converting the whole size of the digital color image into a predetermined size using pixel size conversion, and an ROI extraction step of extracting from the digital color image a region of interest (ROI) necessary for the diagnosis;

a chromatic adaptation transformation step of adjusting the color balance of a data on the digital color image by chromatic adaptation transformation; and a discrimination index calculating step of obtaining a discrimination index using the image after the chromatic adaptation transformation.

The method for analyzing a longitudinal pigmented band on a nail plate and a skin hue may further include a step of determining the presence or absence of a disease using the discrimination index as a threshold value.

The method for analyzing a longitudinal pigmented band on a nail plate and a skin hue may further include a step of analyzing a change in the longitudinal pigmented band on a nail plate or skin hue over time, using a follow-up data of the discrimination index in the same subject to diagnose the outcome of the subject.

In the method for analyzing a longitudinal pigmented band on a nail plate and a skin hue, the chromatic adaptation transformation step may include:

an XYZ transformation step of transforming the linear RGB color space obtained by degamma processing into an XYZ color space;

a coordinate transformation step of transforming an averaged chromaticity coordinate obtained from XYZ parameters of respective pixels in the image expressed in the XYZ color space into a standardized coordinate; and an RGB transformation step of performing gamma processing after transforming the XYZ color space into a linear RGB color space.

In the method for analyzing a longitudinal pigmented band on a nail plate and a skin hue, as the step of obtaining the averaged chromaticity coordinate after the XYZ transformation step, the chromatic adaptation transformation step may include:

a step of assuming an average value of Y obtained by averaging the XYZ parameters as an average luminance signal of Y over the pixels in the whole target region, and a step of setting arbitrary first reference value and second reference value thereover, wherein if the value of the Y average luminance signal is greater than or equal to the first reference value, the average values of X, Y, and Z in the whole target region are calculated with respect to all of the target pixels;

if the value of the Y average luminance signal is smaller than the first reference value, the average values of X, Y, and Z are calculated over pixels whose Y values are greater than the second reference value, while the coordinate transformation step is not performed over pixels whose Y values are equal to or less than the second reference value.

According to the method for analyzing a longitudinal pigmented band on a nail plate and a skin hue of the present invention, the acral lentiginous melanoma, the skin malignant melanoma, or the autoimmune skin disease may be an early stage acral lentiginous melanoma, skin malignant melanoma, or autoimmune skin disease, respectively.

According to the method for analyzing a longitudinal pigmented band on a nail plate and a skin hue, the acral lentiginous melanoma may be selected from nail apparatus melanoma or pigmented Bowen's disease, and the autoimmune skin disease may be a collagenosis including lupus erythematosus, dermatomyositis and scleroderma.

Also, the present invention provides:

a diagnostic method for performing: diagnosis of an acral lentiginous melanoma; diagnosis of a skin cancer such as a malignant melanoma; or diagnosis of an autoimmune skin disease on the skin, including:

an image reading step for reading a color image of a longitudinal pigmented band on a nail plate or a skin site of a subject as a digital color image;

an image processing step of including an image size conversion step of converting the whole size of the digital color image into a predetermined size using pixel size conversion, and an ROI extraction step of extracting from the digital color image a region of interest (ROI) necessary for the diagnosis;

a chromatic adaptation transformation step of adjusting the color balance of the digital color image data by chromatic adaptation transformation; and a discrimination index calculating step of obtaining a discrimination index using the image after the chromatic adaptation transformation.

The diagnostic method may further include a step of determining the presence or absence of a disease, using the discrimination index as a threshold value.

The diagnostic method may further include a step of analyzing a change in the pigmented band on a nail plate or a skin hue over time, using a follow-up data of the discrimination index in the same subject in order to diagnose the outcome.

In the diagnostic device, the chromatic adaptation transformation step may include:

an XYZ transformation step of transforming a linear RGB color space obtained by degamma processing into an XYZ color space;

a coordinate transformation step of transforming an averaged chromaticity coordinate obtained from XYZ parameters of respective pixels in the image expressed in the XYZ color space into a standardized coordinate; and an RGB transformation step of performing gamma processing after transforming the XYZ color space into a linear RGB color space.

In the diagnostic method, as the step of obtaining the averaged chromaticity coordinate after the XYZ transformation step, the chromatic adaptation transformation step may include:

a step of assuming an average value of Y obtained by averaging the XYZ parameters as an average luminance signal of Y over the pixels in the whole target region, and a step of setting arbitrary first reference value and second reference value thereover, wherein if the value of the Y average luminance signal is greater than or equal to the first reference value, the average values of X, Y, and Z in the whole target region are calculated with respect to all of the target pixels, and if the value of the Y average luminance signal is smaller than the first reference value, the average values of X, Y, and Z are calculated over pixels whose Y values are greater than the second reference value, while the coordinate transformation step is not performed over pixels whose Y values are equal to or less than the second reference value.

According to the method for diagnosis of a skin disease of a subject of the present invention, the acral lentiginous melanoma, the skin malignant melanoma, or the autoimmune skin disease may be an early stage acral lentiginous melanoma, skin malignant melanoma, or autoimmune skin disease, respectively.

According to the method for diagnosis of a skin disease of a subject of the present invention, the acral lentiginous melanoma may be selected from nail apparatus melanoma or pigmented Bowen's disease, and the autoimmune skin disease may be a collagenosis including lupus erythematosus, dermatomyositis and scleroderma.

Also, according to the analysis method or diagnostic method of the present invention, the diagnosis may be to determine the presence or absence of a malignant melanoma of a subject.

Further, according to the analysis method or diagnostic method of the present invention, the diagnosis may include a step of analyzing a change in the longitudinal pigmented band on a nail plate or skin hue over time, using a follow-up data of the discrimination index in the same subject to diagnose the outcome of the subject.

The present invention provides a diagnostic device for performing: diagnosis of an acral lentiginous melanoma; diagnosis of a skin cancer such as a malignant melanoma on the skin; or diagnosis of an autoimmune skin disease, including:

an image reading means of reading a color image of a longitudinal pigmented band on a nail plate or a skin site of a subject as a digital color image;

an image processing means including an image size conversion means of converting the whole size of the digital color image into a predetermined size using pixel size conversion, and an ROI extraction means of extracting from the digital color image a region of interest (ROI) necessary for the diagnosis;

a chromatic adaptation transformation means of adjusting the color balance of the digital color image data by chromatic adaptation transformation; and a discrimination index calculating means of obtaining a discrimination index using the image after the chromatic adaptation transformation.

The diagnostic device for performing diagnosis of an acral lentiginous melanoma; diagnosis of a skin cancer such as a malignant melanoma on the skin; or diagnosis of an autoimmune skin disease according to the present invention may further include a diagnostic means of determining whether the longitudinal pigmented band or melanonychia is due to a malignant melanoma or a benign nevus by differentiating the discrimination index as a threshold value.

The diagnostic device for performing diagnosis of an acral lentiginous melanoma; diagnosis of a skin cancer such as a malignant melanoma on the skin; or diagnosis of an autoimmune skin disease according to the present invention may further include a diagnostic means of analyzing and diagnosing a change in the longitudinal pigmented band on a nail plate or skin hue over time, using a follow-up data of the discrimination index in the same subject, to thereby diagnose the outcome of the subject.

According to the diagnostic device, the chromatic adaptation transformation means may include:

an XYZ transformation means of transforming a linear RGB color space obtained by degamma processing into an XYZ color space;

a coordinate transformation means of transforming an averaged chromaticity coordinate obtained from XYZ parameters of respective pixels in the image expressed in the XYZ color space into a standardized coordinate; and an RGB transformation means of performing gamma processing after transforming the XYZ color space into a linear RGB color space.

According to the diagnostic device, as the means of obtaining the averaged chromaticity coordinate after the transformation of the linear RGB color space into the XYZ color space, the chromatic adaptation transformation means may include:

a means of assuming an average value of Y obtained by averaging the XYZ parameters as an average luminance signal of Y over the pixels in the whole target region, and a means of setting arbitrary first reference value and second reference value thereover, wherein if the value of the Y average luminance signal is greater than or equal to the first reference value, the average values of X, Y, and Z in the whole target region are calculated with respect to all of the target pixels, and if the value of the Y average luminance signal is smaller than the first reference value, the average values of X, Y, and Z are calculated over pixels whose Y values are greater than the second reference value, while the averaged chromaticity coordinate is not transformed into the standardized coordinate over pixels whose Y values are equal to or less than the second reference value.

The acral lentiginous melanoma may be selected from nail apparatus melanoma or pigmented Bowen's disease, and the autoimmune skin disease may be a collagenosis including lupus erythematosus, dermatomyositis and scleroderma.

The present invention provides a computer program that causes a computer to function as the above-mentioned diagnostic device for skin disease.

The computer program may further include a computer program to determine the presence or absence of a malignant melanoma for differential diagnosis, and/or a computer program to analyze a change in the same subject over time, to diagnose the outcome in the subject.

Effects of the Invention

According to the analysis method and diagnostic device for diagnosing a skin disease of the present invention, and the computer program that causes the computer to function as the diagnostic device, even inexperienced testers can diagnose it to determine whether longitudinal melanonychias are due to malignant melanomas or benign nevi, without the discrimination index DI greatly varying depending on imaging devices or the testers.

DETAILED DESCRIPTION OF THE PREFERRED EMBODIMENTS

Preferred embodiments of a longitudinal pigmented band on a nail plate and skin hue analysis method and diagnostic device according to the present invention and a computer program that causes a computer to function as the diagnostic device will be described below with reference to the drawings.

The longitudinal pigmented bands on a nail plate appear after a pigmented nevus with an increased melanin deposit, a benign skin tumor, or a malignant skin tumor such as nail apparatus melanoma (subungual melanoma) or pigmented Bowen's disease occurs in a nail matrix; and they also appear after lesions are developed on or in the vicinity of a nail matrix due to skin diseases such as lichen planus and lichen striatus, endocrine abnormalities such as Addison's disease and Cushing's syndrome, metabolic abnormalities such as porphyria and malnutrition, systemic diseases such as Peutz-Jeghers syndrome and pregnancy, bacterial or fungal infectious diseases, internal use of drugs such as anticancer drugs, radiation therapy or ultraviolet therapy to the fingers, and repeated external stimulation thereto. When the acral lentiginous melanoma progresses, not only the nail plate but also the skin color changes. In addition, an autoimmune skin disease is included as an object of the analysis method of the present invention, and the autoimmune skin disease may be, for example, a collagen disease including lupus erythematosus, dermatomyositis, and scleroderma.

In the present specification, the "subject" means a person being tested as long as the longitudinal pigmented band on a nail or melanonychia and skin hue analysis method of the present invention are used in the test. Namely, it is not limited to a patient who has a longitudinal pigmented band on a nail or melanonychia caused by a malignant melanoma or the like, and any healthy person who has a benign longitudinal melanonychia is also included. Moreover, any of males or females and adults, children, elderly or geriatric people are included.

Figure 1:
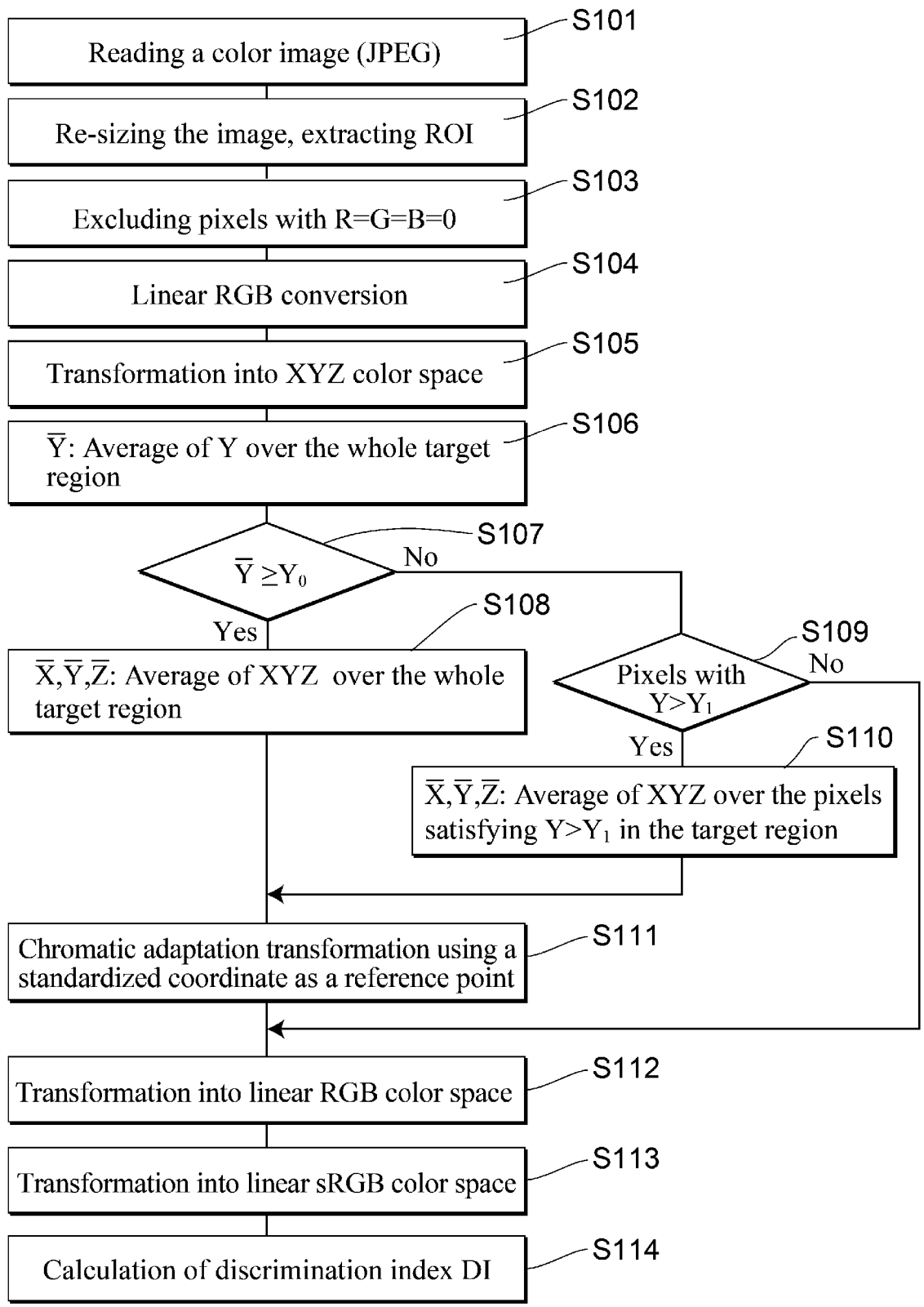
FIG. 1 is a flowchart showing the procedure of a method for analyzing a longitudinal pigmented band on a nail plate and a skin hue according to the present invention.

Then, an example of the longitudinal pigmented band on a nail and skin hue analysis method of the present invention is performed according to a flowchart shown in FIG. 1. Note that the ROI in the present embodiment is a region of image of a nail plate or a skin to be analyzed by processing such as a chromatic adaptation transformation when the image is analyzed in the present embodiment.

Figure 2:
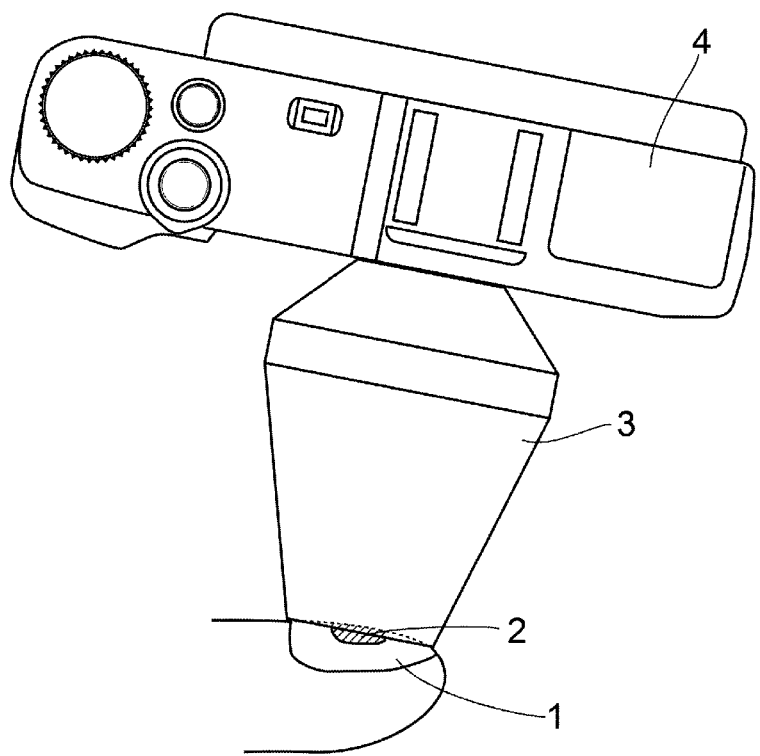
FIG. 2 is a schematic diagram showing an example of photographing a longitudinal melanonychia using a dermoscope and a digital camera.

In the image reading step of step S101, an image reading means reads a color image of a site of the longitudinal melanonychia or skin to be tested, as a digital color image. FIG. 2 shows an apparatus for acquiring the color image, illustrating how a photograph is taken. A longitudinal melanonychia 2 is present in a nail 1 to be imaged. The longitudinal melanonychia 2 can be an acral lentiginous melanoma at an early stage as a diagnosis target of the present embodiment. The acral lentiginous melanoma is selected from nail apparatus melanoma or pigmented Bowen's disease. A dermoscope 3 is mildly pressed against the surface of the nail 1 and a digital camera 4 attached to the dermoscope 3 is used to obtain a color image in JPEG format. It is preferable to apply a transparent gel (not shown) to the surface of the nail 1. This is because by applying the transparent gel, illumination light can be effectively taken into the nail plate and a clear image can be obtained. Alternatively, a printed color photograph may be taken with the digital camera 4 to obtain a digital color image. When the image is taken using the digital camera 4, the color image can be read through, for example, an SD card in which the color image is recorded as a digital color image.

In the image processing step of step S102, an image processing means performs image size conversion of the digital color image (image resizing) and ROI extraction from the nail plate or skin image. The image processing step may include an image size conversion step where the size of one pixel is adjusted by an image size conversion means so that the number of pixels on the short side of the image is set to a predetermined value, and the whole size of the image is set to a predetermined size using pixel size conversion. By this image size conversion, the vertical and horizontal sizes of the digital color image to be processed can be set to a predetermined size. The RGB variable of the pixel whose size has been changed is interpolated using, for example, a bicubic method. The image processing step may further include an ROI extraction step of extracting an ROI necessary for diagnosis from the digital color image by the ROI extraction means. In the ROI extraction step, when extracting the ROI of the nail plate, only the pixels belonging to a portion of the nail plate that is visible on the image are left for analysis. At this time, bubbles contained in the transparent gel on the nail plate, halation, cracks (cloven portions), scratches, etc. are excluded. Also excluded are regions of Hutchinson's symptoms.

Thereafter, using the image that has undergone image size conversion and ROI extraction of the nail plate or skin in step S102, color balance is standardized by chromatic adaptation transformation of RGB variables included in the nail plate or skin ROI. Here, standardization of color balance by chromatic adaptation transformation means performing adjustment in a digital color image obtained under various conditions such as the spectral distribution of illumination light that varies depending on devices used in tests to be standardized, so that the appearance of white is constant by transforming an averaged chromaticity coordinate into a preset chromaticity coordinate as a reference. First, an outline of the standardization will be described. The color balance of the RGB variables included in the JPEG image is determined not only by the state of the photograph but also by the correlated color temperature that varies depending on the device used in the test. The correlated color temperature can be determined using chromaticity coordinates (xbar, ybar) calculated from tristimulus variables (Xbar, Ybar, Zbar) averaged using a given JPEG image. Here, the XYZ variable can be obtained from the RGB variable of each pixel by an operation as described later. Therefore, the color balance of the RGB variable depends on the chromaticity coordinates (xbar, ybar) of a given JPEG image.

Signal processing in any digital camera with the standard color gamut follows the international standard, IEC 61966-2-1 (International standard, IEC 61966-2-1: Multimedia systems and equipment-Colour measurement and management-Part 2-1: Colour management-Default RGB colour spaces-sRGB, 1999). In this international standard, color management-default RGB colour spaces: sRGB, are defined. Its white point is defined by the chromaticity coordinate of $(x_n, y_n)_{D_{65}} = (0.3127, 0.3290)$ calculated via $(X_n, Y_n, Z_n)_{D_{65}}$, where the spectral data of the standard light source $D_{65}$ and the color-matching functions of CIE 1931 Standard Colorimetric System, for λ=380 to 780 nm at 5 nm intervals, are used. Note that the relation $x_n+y_n+z_n=1$ holds.

Figure 3:
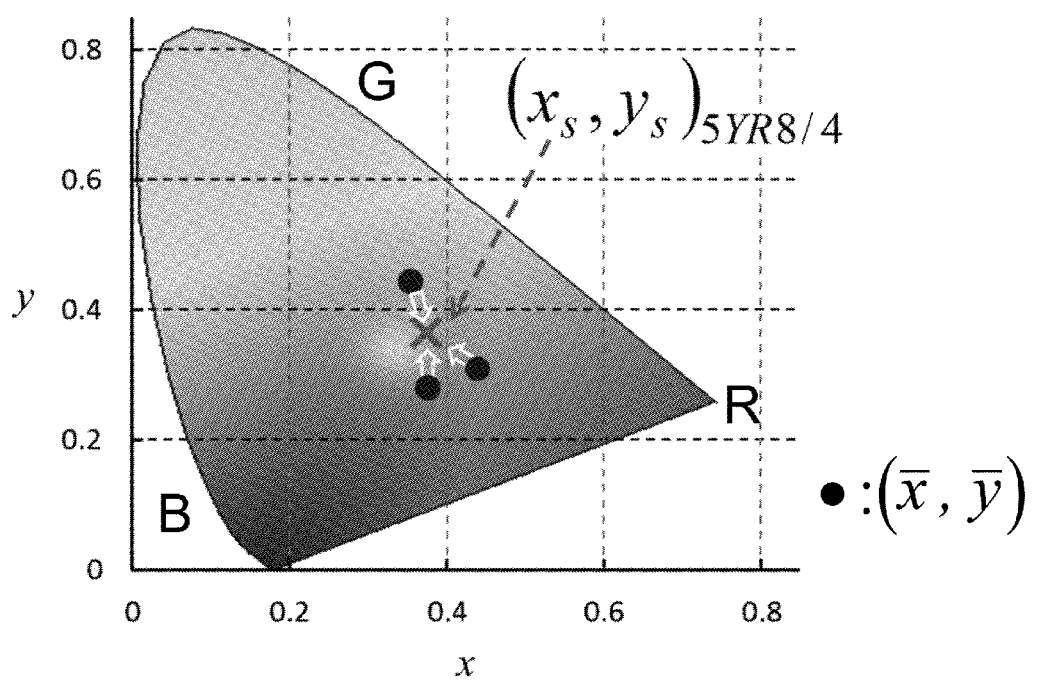
FIG. 3 is a schematic diagram schematically showing standardization of color balance by chromatic adaptation transformation.

In this embodiment, standardization of RGB color balance is performed based on chromatic adaptation transformation before calculating the discrimination index DI value. FIG. 3 is a schematic diagram schematically showing standardization of color balance by chromatic adaptation transformation. In the figure, "R", "G", and "B" indicate the vicinity of red, green, and blue boundaries in the xy chromaticity coordinate, respectively. Because nail plates essentially contain no melanin pigments, they are independent of races. Accordingly, it is possible to set, as a reference chromaticity coordinate, $(x_s, y_s)_{5YR8/4} = (0.3744, 0.3631)$ which serves as a standardized chromaticity coordinate, and is calculated using the reflectance spectra of Caucasian skin under the standard light source $D_{65}$, (JIS Z 8726). The corresponding tristimulus values $(X_s, Y_s, Z_s)_{5YR8/4}$ can be obtained using the spectral data of the standard light source $D_{65}$, the reflectance spectra of Caucasian skin under the standard light source $D_{65}$, JIS Z 8726, and the color-matching functions of the CIE 1931 Standard Colorimetric System. The concrete values of $(X_s, Y_s, Z_s)_{5YR8/4}$ are shown in Equation (8). Here the subscript "5YR8/4" denotes Munsell symbol of the corresponding color sample and the subscript "s" means standard. For any JPEG image, RGB variables are reevaluated using the chromatic adaptation transformation matrix that transforms the chromaticity coordinate ($\bar{x}$, $\bar{y}$) evaluated from the analysis target into the standardized coordinate $(x_s, y_s)_{5YR8/4}$ prior to calculating the discrimination index DI. In FIG. 3, "black circle" indicates chromaticity coordinate ($\bar{x}$, $\bar{y}$) (xbar, ybar), and "x" indicates standardized coordinate $(x_s, y_s)_{5YR8/4}$. Here, the standardized coordinate can be appropriately changed depending on the race of the subject, for example. When, for example, used for diagnosis on the skin, particularly for diagnosis of autoimmune skin diseases such as collagen disease, it is preferable to change the standardized coordinate depending on the race. In this case, if Munsell symbols are used, the standardized coordinate can be set without depending on the standards of respective countries, such as JIS.

Returning to the flowchart shown in FIG. 1, in step S103, the corresponding pixels with R=G=B=0 are excluded from the following consideration.

Steps S104 to S113 are chromatic adaptation transformation steps in which chromatic adaptation transformation means adjusts the color balance of the digital color image data. The chromatic adaptation transformation step may include an XYZ transformation step of transforming a linear RGB color space obtained by degamma processing into an XYZ color space by an XYZ transformation unit; a coordinate transformation step of transforming an averaged chromaticity coordinate obtained from the XYZ parameters of each pixel in the images expressed in an XYZ color space, into standardized coordinates, by a coordinate transformation unit; and an RGB transformation step of performing gamma processing after transforming the XYZ color space into a linear RGB color space by an RGB transformation unit.

In step S104, transformation into a linear RGB color space is performed, using the degamma processing. First, the 8-bit integer RGB variables in nail plate image pixels under consideration are restored to real R'G'B' variables. The R'G'B' variables are reverse-converted into the corresponding linearized variables $R_s G_s B_s$, using the degamma correction. The $R_s G_s B_s$ variables are variables in the standard linear color space sRGB. The R component degamma correction processing is shown in Equation (2). The same processing is performed for the G- and the B-components.

[Equation 1]

$$\begin{pmatrix} R' \\ G' \\ B' \end{pmatrix} = \begin{pmatrix} R/255 \\ G/255 \\ B/255 \end{pmatrix} \quad (1)$$

[Equation 2]

$$R_s = \begin{cases} R'/12.92 & R' \leq 0.04045 \\ ((R'+0.055)/1.055)^{2.4} & R' > 0.04045 \end{cases} \quad (2)$$

In the XYZ transformation step of step S105, the $R_s G_s B_s$ variables in the sRGB color space are transformed into the corresponding tristimulus values, i.e, XYZ variables in the XYZ color space, based on the Equation (3). Equation (3) is derived assuming a white point $D_{65}$. The tristimulus variables are averaged over the pixel of interest, resulting in (Xbar, Ybar, Zbar) $D_{65}$. As shown in step S106, Ybar is assumed as a Y average luminance signal, and subsequent processing is determined based on the value of Ybar.

[Equation 3]

$$\begin{pmatrix} X \\ Y \\ Z \end{pmatrix}_{D_{65}} = \begin{pmatrix} 0.4124 & 0.3576 & 0.1805 \\ 0.2126 & 0.7152 & 0.0722 \\ 0.0193 & 0.1192 & 0.9505 \end{pmatrix} \begin{pmatrix} R_s \\ G_s \\ B_s \end{pmatrix} \quad (3)$$

Figure 4:
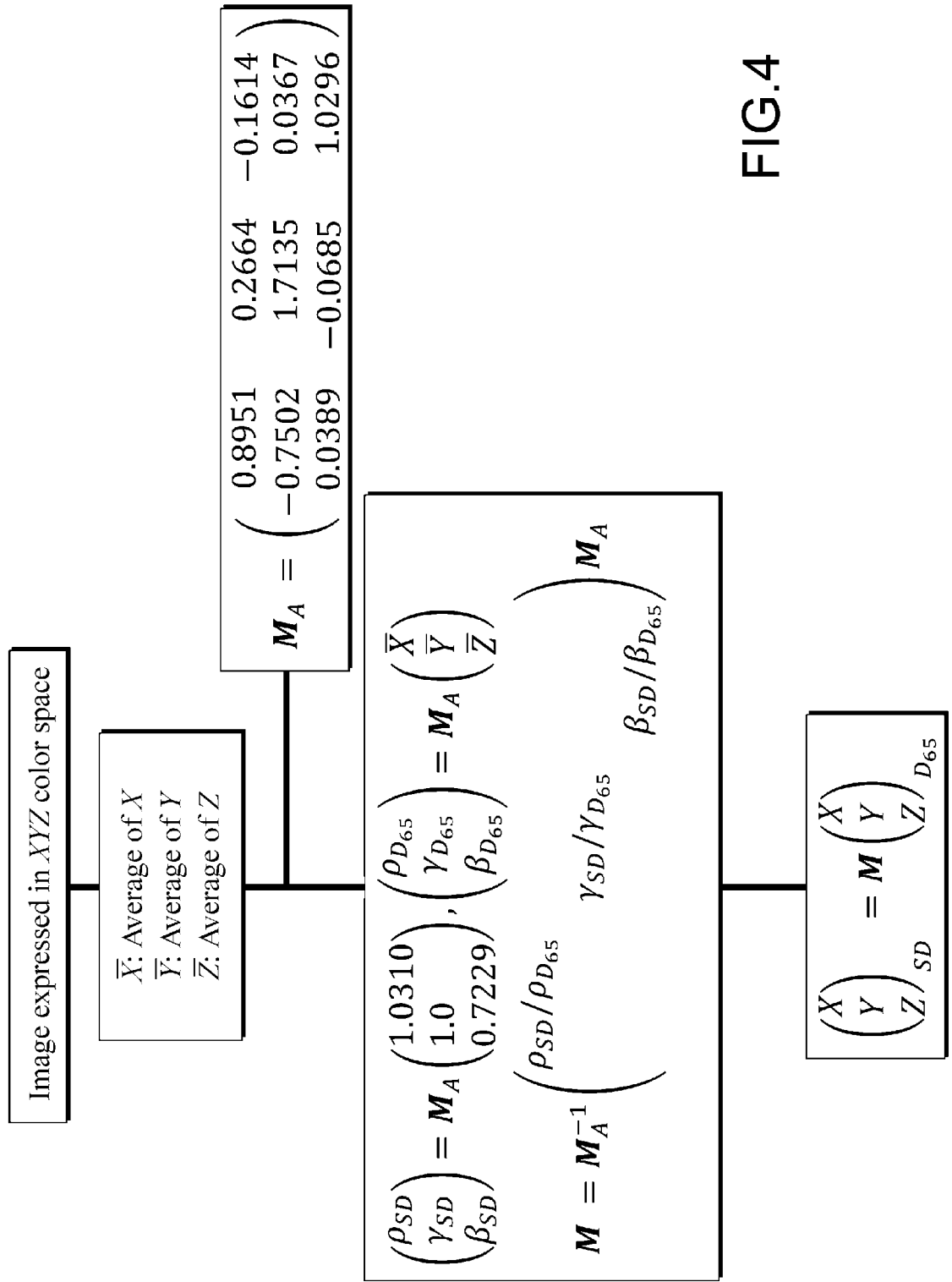
FIG. 4 is a flowchart showing the procedure of a chromatic adaptation transformation algorithm.

First, the coordinate transformation step in step S111 will be described. In step S111, the coordinate transformation means executes a chromatic adaptation transformation algorithm using the standardized coordinate as a reference point based on Equation (4). FIG. 4 shows a flowchart of the chromatic adaptation transformation algorithm. Here, the transformation matrix M is expressed by Equation (5). ($\rho_{SD}$, $\gamma_{SD}$, $\beta_{SD}$) and ($\rho_{D65}$, $\gamma_{D65}$, $\beta_{D65}$) are obtained by Equation (6). The specific value of $(X_s, Y_s, Z_s)_{5YR8/4}$ is shown in Equation (8). The transformation matrix $M_A$ is assumed to be given by the Bradford transformation matrix shown in Equation (7) and FIG. 4.

[Equation 4]

$$\begin{pmatrix} X \\ Y \\ Z \end{pmatrix}_{5YR8/4} = M \begin{pmatrix} X \\ Y \\ Z \end{pmatrix}_{D65} \quad (4)$$

[Equation 5]

$$M = M_A^{-1} \begin{pmatrix} \rho_{SD}/\rho_{D65} & & \\ & \gamma_{SD}/\gamma_{D65} & \\ & & \beta_{SD}/\beta_{D65} \end{pmatrix} M_A \quad (5)$$

[Equation 6]

$$\begin{pmatrix} \rho_{SD} \\ \gamma_{SD} \\ \beta_{SD} \end{pmatrix} = M_A \begin{pmatrix} X_s \\ Y_s \\ Z_s \end{pmatrix}_{5YR8/4}, \quad \begin{pmatrix} \rho_{D65} \\ \gamma_{D65} \\ \beta_{D65} \end{pmatrix} = M_A \begin{pmatrix} X\,\text{bar} \\ Y\,\text{bar} \\ Z\,\text{bar} \end{pmatrix}_{D65} \quad (6)$$

[Equation 7]

$$M_A = \begin{pmatrix} 0.8951 & 0.2664 & -0.1614 \\ -0.7502 & 1.7135 & 0.0367 \\ 0.0389 & -0.0685 & 1.0296 \end{pmatrix} \quad (7)$$

[Equation 8]

$$\begin{pmatrix} X_s \\ Y_s \\ Z_s \end{pmatrix}_{5YR8/4} = \begin{pmatrix} 1.0310 \\ 1 \\ 0.7229 \end{pmatrix} \quad (8)$$

Returning to step S107, description will be given. In step S107, if the value of the averaged luminance signal Ybar ($\bar{Y}$) is greater than or equal to the first reference value $Y_0$, that is, if Ybar≥$Y_0$, the process proceeds to step S108, and in all the pixels under consideration, the X,Y,Z average values: Xbar, Ybar, and Zbar are calculated in the whole target region, and the process proceeds to the coordinate transformation step in step S111 described above. If the value of the average luminance signal Ybar is smaller than the first reference value $Y_0$, that is, if Ybar<$Y_0$, the process proceeds to step S109, and processing is further determined according to the magnitude of the Y value of each pixel. That is, if the value of Y is larger than the second reference value $Y_1$, that is, if Y>$Y_1$, the process proceeds to step S110, and the average values of X, Y, and Z: Xbar, Ybar, and Zbar of the pixels that satisfy Y>$Y_1$ in the target region are calculated, and the process proceeds to the coordinate transformation step in step S111 described above. A pixel whose Y value is less than or equal to the second reference value $Y_1$, that is, a pixel that satisfies Y≤$Y_1$, does not undergo the coordinate transformation processing in step S111, and is processed directly as $(X, Y, Z)_{5YR8/4} = (X, Y, Z)_{D65}$, and the process proceeds to step S112.

That is, the chromatic adaptation transformation step includes, as a step of obtaining an averaged chromaticity coordinate after the XYZ transformation step, a step of assuming the average value of Y obtained by averaging the XYZ parameters over the pixels in the whole target region as an average luminance signal of Y; a step of setting an arbitrary first reference value $Y_0$ and second reference value $Y_1$ thereover. If the average luminance signal value of Y is greater than or equal to the first reference value $Y_0$ ("Yes" condition in step S107), an average value of X, Y, and Z in the whole target region is calculated for all the target pixels (step S108), and if the value of the Y average luminance signal is smaller than the first reference value $Y_0$ ("No" condition in step S107), the average value of X, Y and Z is calculated over pixels whose Y value is larger than the second reference value $Y_1$ ("Yes" condition in step S109), and no coordinate transformation step is performed over pixels whose Y value is below the second reference value ("No" condition in step S109).

The values of the first reference value $Y_0$ and the second reference value $Y_1$ can be arbitrarily set. For example, the value of the first reference value $Y_0$ may be 0.18 and the value of the second reference value $Y_1$ may be 0.2, based on an actual image obtained from a subject described in the following embodiments. In the case of a nail plate, a dark pixel that is close to black has a large noise, so that the chromatic adaptation transformation thereof may increase a noise content. Thus, in the case of a nail plate, the luminance signal of a pixel that is not subject to calculation has a relatively small value. Thus, by excluding pixels whose luminance signals have a predetermined value or less, it is possible to reduce the amount of information to be calculated and improve the calculation speed of analysis. Furthermore, the colors necessary for diagnosis can be sufficiently extracted. The first reference value $Y_0$ and the second reference value $Y_1$ are preferably determined by examining a sufficient number of cases.

In the RGB transformation step of step S112, the RGB transformation means transforms the XYZ variable, which is a tristimulus variable of the pixel of the obtained nail plate or skin ROI image, into an $R_s G_s B_s$ variable based on Equation (9), thus performing transformation to linear RGB color space. In step S113, transformation to the sRGB color space is performed. That is, after performing gamma correction according to Equation (10), the corresponding RGB integer variable is calculated using Equation (11). Expressions (10) and (11) show only the R component. The same processing is performed for the G component and the B component.

[Equation 9]

$$\begin{pmatrix} R_s \\ G_s \\ B_s \end{pmatrix} = \begin{pmatrix} 3.2406 & -1.5372 & -0.4986 \\ -0.9689 & 1.8758 & 0.0415 \\ 0.0557 & -0.2040 & 1.0570 \end{pmatrix} \begin{pmatrix} X \\ Y \\ Z \end{pmatrix}_{5YR8/4} \quad (9)$$

[Equation 10]

$$R' = \begin{cases} 12.92 R_s & R_s \leq 0.00313 \\ 1.055 R_s^{1/2.4} - 0.055 & R_s > 0.00313 \end{cases} \quad (10)$$

[Equation 11]

$$R = \text{int}(255 R') \quad (11)$$

Regarding the de-gamma correction of Equation (2) and the gamma correction of Equation (10), for example, the following documents can be referred to. International standard, IEC 61966-2-1: Multimedia systems and equipment-Colour measurement and management-Part 2-1: Colour management-Default RGB colour spaces-sRGB, 1999.

Regarding transformation from the linear RGB color space into the XYZ color space of Equation (3) and transformation from the XYZ color space to the linear RGB color space of Equation (9), the following documents, for example, can be referred to.

1. International standard, IEC 61966-2-1: Multimedia systems and equipment-Colour measurement and management-Part 2-1: Colour management-Default RGB colour spaces-sRGB, 1999.
2. International recommendation, ITU-R BT. 709-7: Parameter values for the HDTV standards for production and international programme exchange, 2002.

In the discrimination index calculation step of step S114, the discrimination index can be obtained by a discrimination index calculation means using the image after chromatic adaptation transformation obtained according to the above flow. The calculation method described in the Nonpatent document 1 and the Patent document 1 which the present inventors developed can be used for the calculation method of the discrimination index. Briefly, the RGB variable value of each pixel in the dermoscopic image of a longitudinal melanonychia is assumed as a three-dimensional vector in the RGB space, and the discrimination index DI value is obtained from the latitude variable $\theta i$ and the longitude variable $\varphi i$, using Equation (12).

[Equation 12]

$$DI = \sqrt{\frac{1}{N}\sum_{i=1}^{N}\left[(\phi_i - \overline{\phi})^2 + (\theta_i - \overline{\theta})^2\right]} \qquad (12)$$

In the diagnosing step, it is possible to determine whether a longitudinal melanonychia is a malignant melanoma or a benign nevus by differentiating the discrimination index DI value calculated by the above method as a threshold. It can be determined if the value of the discrimination index DI is larger than the threshold serving as a boundary, it is an early nail apparatus melanoma, and if the value is smaller than the threshold, it is a benign nevus.

The skin disease diagnostic device according to the present embodiment may include the above-described image reading means, image processing means, discrimination index calculation means, and diagnosis means.

Figure 5:
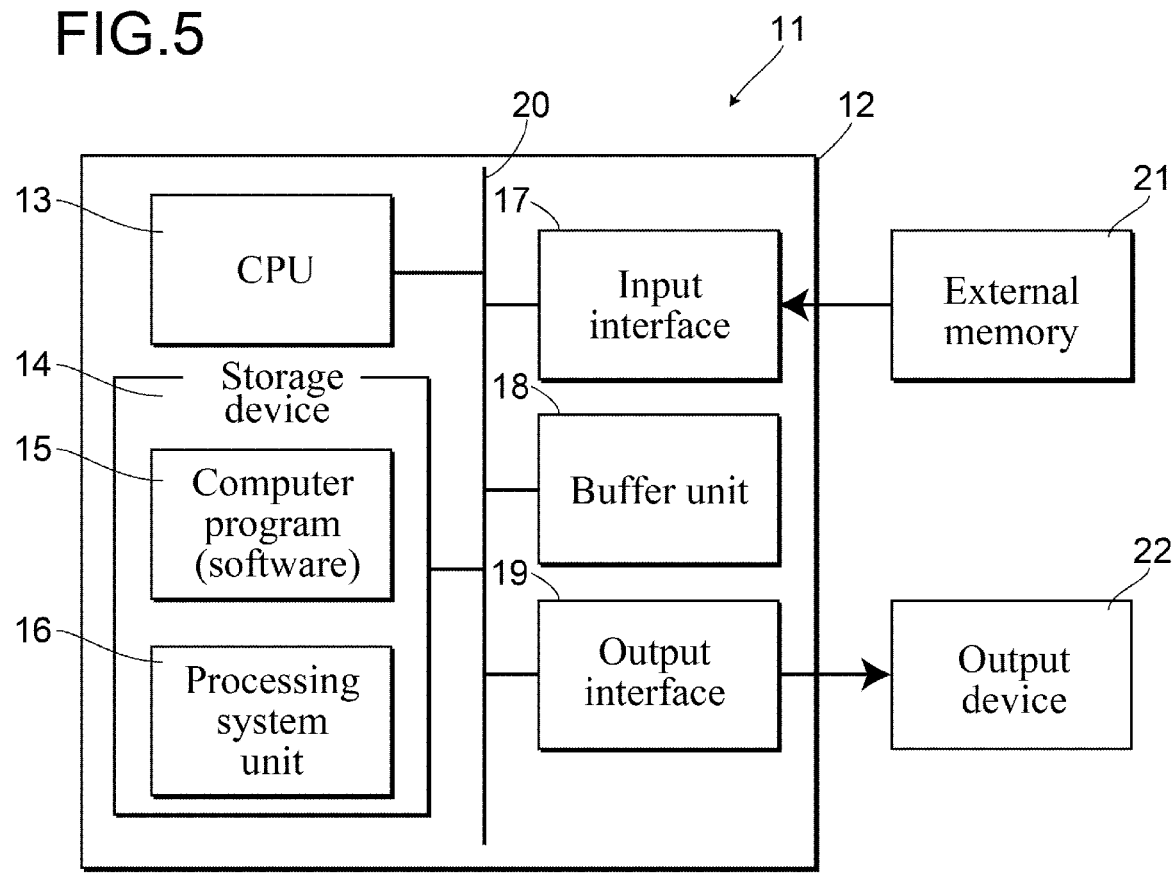
FIG. 5 is a block diagram schematically showing an example in which a computer program is installed in a computer so that the computer functions as a diagnostic device of a longitudinal melanonychia and a skin disease according to the present invention.
Figure 6A:
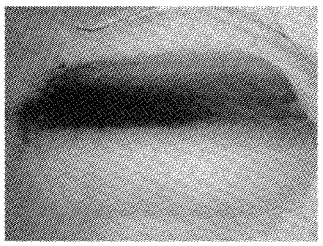
FIG. 6A to 6F denote drawings whose original drawings are color photographs of a longitudinal melanonychia, in which 6A denotes a JPEG image of a nail apparatus melanoma before standardization of color balance, 6B and 6C denote those of a benign nevi, while 6D, 6E, and 6F respectively denote a color image obtained by extracting from the images of 6A, 6B, and 6C by a tester a part corresponding to the nail plate, and then standardizing its color balance by the analysis method of a longitudinal melanonychia of the present invention.
Figure 6B:
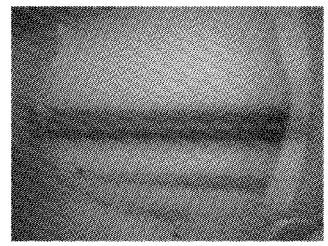
Figure 6C:
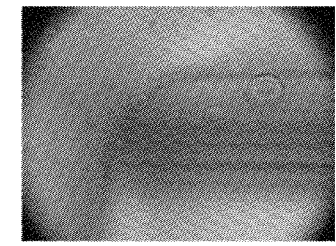
Figure 6D:
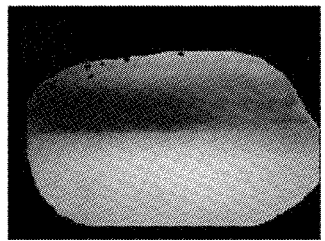
Figure 6E:
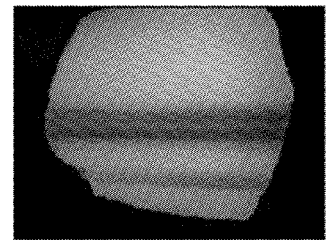
Figure 6F:
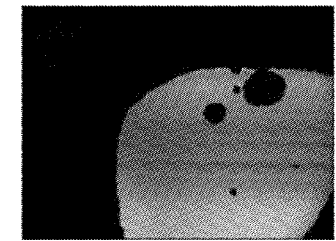

FIG. 5 is a block diagram schematically showing an example in which a computer program is installed so that the computer functions as a skin disease diagnostic device of the present invention. Such diagnostic device 11 is realized, for example, by installing a computer program (software) 15 in a storage device 14 including, for example, an HDD (hard disk drive) in a computer 12 having a CPU (central processing unit) 13. The function of the diagnostic device 11 is realized by the cooperation of the hardware resources of the computer 12 and the software of the computer program 15. The computer program may include: a computer program for differentiating the presence or absence of a malignant melanoma, and/or a computer program for analyzing data of changes over time obtained from follow-up of the same subject to diagnose the outcome of the subject.

The source code of the computer program 15 may be recorded on a recording medium (not shown) readable by the computer 12. Thus, there can be provided a portable recording medium which has recorded a computer program for diagnosing a longitudinal melanonychia and a skin disease using the above-mentioned analysis method. Examples of the recording medium include a magnetic tape, a magnetic disk such as FD and HDD, an optical disk such as CD-ROM, MO, and DVD, and a recording medium using a semiconductor memory such as a USB memory.

The CPU 13 executes various arithmetic processes based on the computer program 15. The computer program 15 may be taken into the storage device 14 from the above portable recording medium, or may be taken into the storage device 14 from a computer network such as a LAN (Local Area Network) or the Internet. The CPU 13 and the storage device 14 are connected to each other by a bus 20, for example. An input interface 17, a buffer unit 18, and an output interface 19 are further connected to the bus 20.

The input interface 17 functions as a kind of interface for inputting an image to the diagnostic device 11 and is connected to an external memory 21. The external memory 21 is, for example, a CF card, SD card, smart media, USB memory or the like, and may be a memory mounted on an external device (not shown).

The buffer unit 18 is constituted of a RAM, for example, and stores an image input from the input interface 17. The stored image is used for processing in a later-described processing system unit 16 in the storage device 14 connected to the buffer unit 18 via the bus 20.

The output interface 19 is connected to an output device 22 such as a display, for example. Via this output interface 19, an image captured by the diagnostic device 11, a result of the calculation by the computer program 15, etc., are displayed on the output device 22.

In addition, for example, since the progression of nail apparatus melanoma is relatively slow, it is useful to follow up the progression of longitudinal melanonychia. Especially in pediatric subjects, experience shows that some of longitudinal melanonychias disappeared during the follow-up, although it had been strongly speculated that the longitudinal melanonychias were due to malignant melanomas, revealing that they were not longitudinal melanonychias due to malignant melanomas. Then, in order to avoid unnecessary treatment being performed to such subjects, the present invention enables an analysis for diagnosis of outcome to be performed, using observation data of the discrimination index DI value calculated based on the present embodiment for the data obtained by the follow-up observation of the same subjects. The diagnostic device 11 may be configured to allow a computer program 15 to create a graph indicating a time on a horizontal axis and a discrimination index DI value on a vertical axis, for example, and then display the graph on an output device 22 via an output interface 19. Testers can perform analysis for follow-up observation of the longitudinal pigmented bands on a nail plate or the skin hue by referring to the graph displayed on the output device 22.

In the meantime, whilst the output device 22 is disposed outside the diagnostic device 11 in FIG. 5, the output device 22 may be included in the diagnostic device 11 and provided integrally therewith.

The processing system unit 16, being arranged in the storage device 14, can perform resizing of the image, extraction of the ROI of the nail plate or skin, standardization of the color balance by chromatic adaptation transformation, etc., using images stored in the buffer unit 18, through an arithmetic processing based on the computer program 15. Extraction of the ROI of the nail plate or skin may be automatically performed using a means having an automatic extraction function using a known image recognition technique such as outline extraction or pattern recognition. Alternatively, an image may be displayed on the output device 22 and extracted manually (manual operation) using an input device (not shown) such as a mouse via the GUI of the computer program 15, or extracted automatically as described above, followed by correcting the extracted one manually while viewing the image on the screen of the output device 22.

Examples of target diseases: for analysis of a longitudinal pigmented band on a nail plate or melanonychia for diagnosis of an acral lentiginous melanoma or for acquisition of data for diagnosis of acral lentiginous melanoma; or for diagnosis of acral lentiginous melanoma include: lesions after occurrence of a malignancy in a nail matrix, such as nail apparatus melanoma (subungual melanoma) and pigmented Bowen's disease; skin diseases such as lichen planus and lichen striatus; endocrine abnormalities such as Addison's disease and Cushing syndrome; metabolic disorders such as porphyria and malnutrition; systematic diseases such as Peutz-Jeghers syndrome and pregnancy; bacterial and fungal infections; lesions caused in or in the vicinity of a nail matrix due to internal use of drugs such as anticancer drugs, radiation therapy or UV therapy to fingers, and repeated external stimulation. Among these, malignant melanomas such as nail apparatus melanoma (subungual melanoma) and pigmented Bowen's disease are preferably targeted, and nail apparatus melanoma (subungual melanoma) is more preferably targeted.

WORKING EXAMPLES

All documents mentioned herein are hereby incorporated by reference in their entirety. Examples described herein are illustrative of embodiments of the invention and should not be construed as limiting the scope of the invention.

In order to evaluate the difference in the diagnostic performance of the discrimination index DI with respect to the difference in the extracted nail plate region, a blind test was performed. Five testers, A, B, C, D and E, conducted a blind test. Each tester extracted the nail plate images from thirty-one JPEG images including six JPEG images of nail apparatus melanoma and 25 JPEG images of benign longitudinal melanonychia according to the protocol described below, and calculated respective discrimination index DI values, based on the images of the nail plate extracted by each tester.

The color images of the longitudinal melanonychia were taken, using a dermoscope (Derma 9500, manufactured by Derma Medical Inc.) with a digital camera (Coolpix E990, manufactured by Nikon Corp., or PowerShot A620, manufactured by Canon Inc.) attached thereto, or a dermoscope (Dermlite II Fluid, manufactured by 3Gen Inc.) with a digital video camera recorder (HDR-HC3, manufactured by Sony Corp.) attached thereto. As a transparent gel, KY jelly manufactured by Johnson & Johnson was used.

The following contents were presented to the testers as a guideline (protocol) for extracting the nail plate images.
(1) The number of pixels along the short side of the JPEG image should be set to 205 by resizing the size of one pixel. The RGB variables of the resized pixels should be interpolated using the bicubic method.
(2) Only the pixels that belong to the nail plate and are visible on the images should be left for analysis. However, air bubbles contained in the gel on the nail plate, halation, cracks (cloven portions), scratches, etc. should be excluded.
(3) The regions of Hutchinson's symptoms should not be included in the analysis, either.

In step S102, extraction of the nail plate images was performed manually as described above. In step S107, the first reference value $Y_0$ was set to 0.18, and in step S108, the second reference value $Y_1$ was set to 0.2.

FIG. 6 shows black and white views of color photographs of longitudinal melanonychias, in which (a), (b) and (c) are JPEG images prior to standardization of color balance, and (a) shows a nail apparatus melanoma, while (b) and (c) show a benign nevus. (d), (e) and (f) show color images obtained by allowing a tester A to extract the nail plate parts from the images of (a), (b), and (c), respectively, and subjecting them to the standardization of color balance, using the analysis method of longitudinal melanonychia according to the present embodiment.

The image in (a) has a whitish color, and the image in (b) has a bluish color. The hues of (d) and (e) differed greatly from the hues of (a) and (b), respectively, but the hue of (f) was close to the hue of (c). The hues of (d), (e) and (f) were close to those seen with the naked eye.

Figure 7:
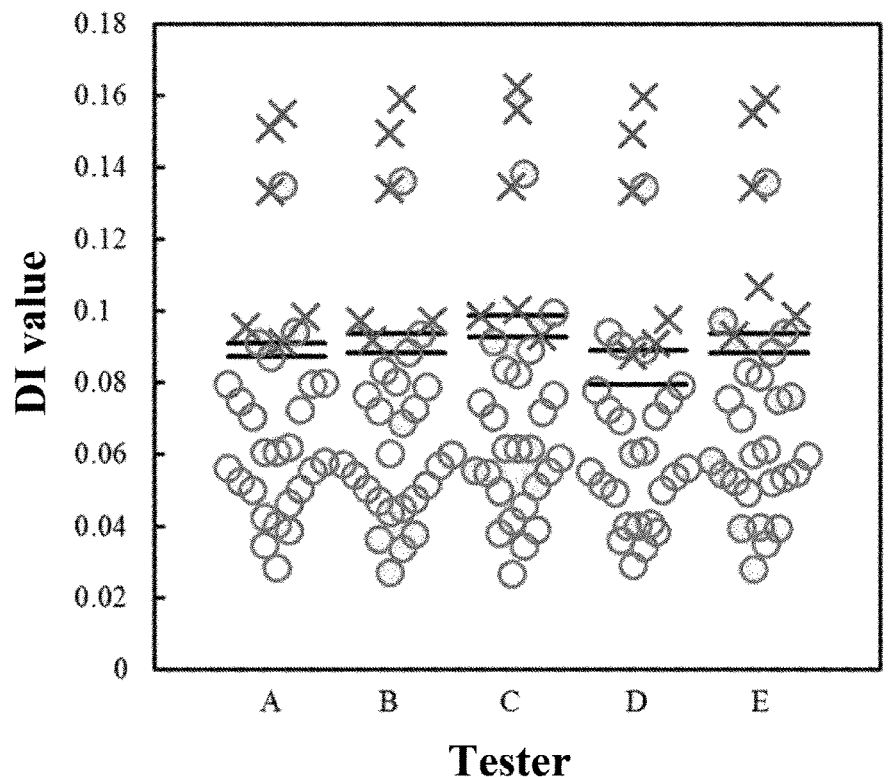
FIG. 7 is a diagram showing, as a comparative example, a result of calculating a discrimination index DI value without performing the color balance standardization by the analysis method of a longitudinal melanonychia of the present invention.

FIG. 7 shows, as a comparative example, the result of calculating the discrimination index DI value without performing standardization of color balance by the analysis method of longitudinal melanonychia according to the present embodiment. The number of the discrimination index DI values calculated by testers A, B, C, D, and E was 31 each. In the figure, "X" denotes the results of calculating the discrimination index DI values from the images of the nail apparatus melanomas, and "white circle" denotes the result of calculating the discrimination index DI values from the images of the benign nevi. The images with the higher color diversity tended to indicate the higher discrimination index DI values. In the comparative example, for each tester A, B, C, D and E, the specificity when the threshold value was fixed so as to obtain the highest specificity when fixing for the sensitivity of 100%. As a result, the specificities were 88%, 92%, 92%, 84%, and 88%, respectively. "Sensitivity" means the probability of correctly diagnosing an early nail apparatus melanoma as positive, and "specificity" means the probability of correctly diagnosing a benign nevus as negative. The "threshold value" is a boundary value for diagnosing a lesion having an index value higher than or equal to that as positive and diagnosing a lesion having an index value less than that as negative. The sensitivity, specificity and threshold were determined by ROC Analysis (Receiver Operating Characteristic Analysis). Here, the denotation of $DI_{th}$ (100, 92) means that the diagnostic performance at the threshold is 100% sensitivity and 92% specificity. In FIG. 7, for each tester A, B, C, D and E, upper and lower solid lines respectively represent a threshold value giving the highest specificity and the one giving the second highest specificity that are obtained when the sensitivity is fixed at 100%. That is, the result was that the value of the discrimination index DI varied depending on the tester, and the threshold value used as a reference when determining whether the longitudinal melanonychia is due to malignant melanoma or benign nevus, and the diagnostic result based on the same, differed depending on the tester.

Figure 8:
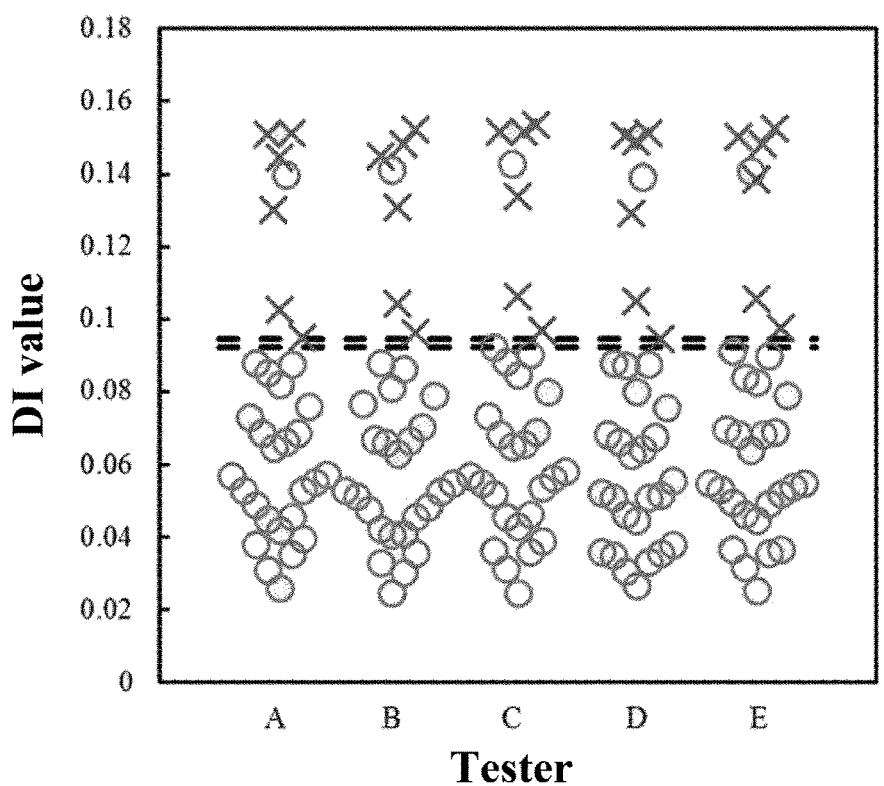
FIG. 8 is a diagram illustrating a result of calculating a discrimination index DI value after standardizing the color balance by the longitudinal melanonychia analysis method according to the present invention.

FIG. 8 shows the result of calculating the discrimination index DI value after standardizing the color balance by the analysis method of longitudinal melanonychia according to the present embodiment. In the figure, "X" denotes the results of calculating the discrimination index DI values from the images of the nail apparatus melanomas, and "white circle" denotes the results of calculating the discrimination index DI values from the images of benign nevi. Table 1 shows two types of values, threshold values $DI_{th}$ (100, 96) and $DI_{th}$ (100, 92), for each of the testers A, B, C, D, and E.

As can be seen from FIG. 8 and Table 1, whilst each tester A, B, C, D, and E had different two types of thresholds, there could be obtained a certain band of threshold value $DI_{th}$ common to each of A, B, C, D and E, i.e., 0.0922<$DI_{th}$≤0.0947 at which a diagnostic result with a sensitivity of 100% and a specificity of 96% was realized. In FIG. 8, a broken line indicates a threshold band common to each of the testers A, B, C, D, and E. According to the analysis method of the present embodiment, such common threshold band can be applied without depending on testers and imaging devices. In the present embodiment, the correct diagnosis rate was 96.8%. The "correct diagnosis rate" means the probability of correctly diagnosing an early nail apparatus melanoma as positive and correctly diagnosing a benign nevus as negative.

The specificity and correct diagnosis rate of the present working example turned out to be higher than the specificity and correct diagnosis rate of the comparative example. From this result, it can be said that the difference of color diversity is one of the most important features in diagnosing early nail apparatus melanoma from the longitudinal melanonychia.

Further, according to the analysis method of the present example, it is possible to suppress the influences upon the discrimination index DI by the differences in the nail plate region extracted for analysis and the variations in color balance in each model that are latent in the input color digital images such as JPEG images, according to the model of the dermoscope 3 or that of the digital camera 4. Thus, according to the analysis method of this embodiment, even an inexperienced tester can make a diagnosis to determine whether the subject's longitudinal melanonychia is due to a malignant melanoma.

TABLE 1

| | $DI_{th}$ (SE, SP) SE, SP in % | | | | |
|---|---|---|---|---|---|
| | Tester A | Tester B | Tester C | Tester D | Tester E |
| $DI_{th}$ (100, 92) | 0.0878 | 0.0880 | 0.0922 | 0.0880 | 0.0912 |
| $DI_{th}$ (100, 96) | 0.0949 | 0.0963 | 0.0968 | 0.0947 | 0.0974 |

Although the present invention has been described based on the embodiments and examples, the present invention can be modified in various ways. For example, although the computer 12 is shown as the diagnostic device 11 in the present embodiment, a tablet terminal, a smartphone, or the like may be employed to perform the processing. Further, the configuration of the computer 12 as the diagnostic device 11 is not limited to the configuration of FIG. 5.

EXPLANATION OF SYMBOLS

11 diagnostic device
15 computer program
$Y_0$ first reference value
$Y_1$ second reference value

The invention claimed is:

1. A method for analyzing a longitudinal pigmented band on a nail plate or a skin hue for performing: diagnosis of an acral lentiginous melanoma; diagnosis of a skin cancer including a malignant melanoma on the skin; or diagnosis of an autoimmune skin disease, comprising:
    an image reading step of reading a color image of a longitudinal pigmented band on a nail plate or a skin site of a subject as a digital color image;
    an image processing step of including an image size conversion step of converting the whole size of the digital color image into a predetermined size using pixel size conversion, and an ROI extraction step of extracting from the digital color image a region of interest (ROI) necessary for the diagnosis;
    a chromatic adaptation transformation step of adjusting the color balance of a data on the digital color image by chromatic adaptation transformation; and
    a discrimination index calculating step of obtaining a discrimination index using the image after the chromatic adaptation transformation.

2. The method for analyzing a longitudinal pigmented band on a nail plate or a skin hue according to claim 1, further comprising a step of determining the presence or absence of a disease using the discrimination index as a threshold value.

3. The method for analyzing a longitudinal pigmented band on a nail plate or a skin hue according to claim 1, further comprising a step of analyzing a change in the longitudinal pigmented band on a nail plate or skin hue over time, using a follow-up data of the discrimination index in the same subject to diagnose the outcome of the subject.

4. The method for analyzing a longitudinal pigmented band on a nail plate or a skin hue according to claim 1, wherein the chromatic adaptation transformation step includes:
    an XYZ transformation step of transforming the linear RGB color space obtained by degamma processing into an XYZ color space;
    a coordinate transformation step of transforming an averaged chromaticity coordinate obtained from XYZ parameters of respective pixels in the image expressed in the XYZ color space into a standardized coordinate; and
    an RGB transformation step of performing gamma processing after transforming the XYZ color space into a linear RGB color space.

5. The method for analyzing a longitudinal pigmented band on a nail plate or a skin hue according to claim 4, wherein as the step of obtaining the averaged chromaticity coordinate after the XYZ transformation step, the chromatic adaptation transformation step includes:
    a step of assuming an average value of Y obtained by averaging the XYZ parameters as an average luminance signal of Y over the pixels in the whole target region, and a step of setting arbitrary first reference value and second reference value thereover, wherein
    if the value of the Y average luminance signal is greater than or equal to the first reference value, the average values of X, Y, and Z in the whole target region are calculated with respect to all of the target pixels;
    if the value of the Y average luminance signal is smaller than the first reference value, the average values of X, Y, and Z are calculated over pixels whose Y values are greater than the second reference value, while the coordinate transformation step is not performed over pixels whose Y values are equal to or less than the second reference value.

6. The method for analyzing a longitudinal pigmented band on a nail plate or a skin hue according to claim 1, wherein the acral lentiginous melanoma, the skin malignant melanoma, or the autoimmune skin disease is an early stage acral lentiginous melanoma, skin malignant melanoma, or autoimmune skin disease, respectively.

7. The method for analyzing a longitudinal pigmented band on a nail plate or a skin hue according to claim 1, wherein the acral lentiginous melanoma is selected from nail apparatus melanoma or pigmented Bowen's disease, and the autoimmune skin disease is a collagenosis including lupus erythematosus, dermatomyositis and scleroderma.

8. A diagnostic device for performing: diagnosis of an acral lentiginous melanoma; diagnosis of a skin cancer including a malignant melanoma on the skin; or diagnosis of an autoimmune skin disease, comprising:
- an image reading means of reading a color image of a longitudinal pigmented band on a nail plate or a skin site of a subject as a digital color image;
- an image processing means including an image size conversion means of converting the whole size of the digital color image into a predetermined size using pixel size conversion, and an ROI extraction means of extracting from the digital color image a region of interest (ROI) necessary for the diagnosis;
- a chromatic adaptation transformation means of adjusting the color balance of the digital color image data by chromatic adaptation transformation; and
- a discrimination index calculating means of obtaining a discrimination index using the image after the chromatic adaptation transformation.

9. The diagnostic device according to claim 8, further comprising a diagnostic means of determining whether the longitudinal pigmented band is due to a malignant melanoma or a benign nevus by differentiating the discrimination index as a threshold value.

10. The diagnostic device according to claim 8, further comprising a diagnostic means of diagnosing the outcome of the subject by analyzing a change in the longitudinal pigmented band on a nail plate or skin hue over time, using a follow-up data of the discrimination index in the same subject.

11. The diagnostic device according to claim 8, wherein the chromatic adaptation transformation means includes:
- an XYZ transformation means of transforming a linear RGB color space obtained by degamma processing into an XYZ color space;
- a coordinate transformation means of transforming an averaged chromaticity coordinate obtained from XYZ parameters of respective pixels in the image expressed in the XYZ color space into a standardized coordinate; and
- an RGB transformation means of performing gamma processing after transforming the XYZ color space into a linear RGB color space.

12. The diagnostic device according to claim 11, wherein as the means of obtaining the averaged chromaticity coordinate after the transformation of the linear RGB color space into the XYZ color space, the chromatic adaptation transformation means includes:
- a means of assuming an average value of Y obtained by averaging the XYZ parameters as an average luminance signal of Y over the pixels in the whole target region, and a means of setting arbitrary first reference value and second reference value thereover, wherein
- if the value of the Y average luminance signal is greater than or equal to the first reference value, the average values of X, Y, and Z in the whole target region are calculated with respect to all of the target pixels, and
- if the value of the Y average luminance signal is smaller than the first reference value, the average values of X, Y, and Z are calculated over pixels whose Y values are greater than the second reference value, while the averaged chromaticity coordinate is not transformed into the standardized coordinate over pixels whose Y values are equal to or less than the second reference value.

13. The diagnostic device according to claim 8, wherein the acral lentiginous melanoma is selected from nail apparatus melanoma or pigmented Bowen's disease, and the autoimmune skin disease is a collagenosis including lupus erythematosus, dermatomyositis and scleroderma.

14. A non-transient and machine-readable recording medium recording a computer program that causes a computer to function as the diagnostic device for a longitudinal pigmented band on a nail or skin disease set forth in claim 8.

* * * * *